US00PP23343P3

(12) United States Plant Patent
Suphachadiwong

(10) Patent No.: US PP23,343 P3
(45) Date of Patent: Jan. 22, 2013

(54) ***VANDA* PLANT NAMED 'SPCDW0902'**

(50) Latin Name: ***Vanda* hybrid**
Varietal Denomination: SPCDW0902

(75) Inventor: Thumrong Suphachadiwong, Chonburi (TH)

(73) Assignee: Suphachatwong (TH)

( * ) Notice: Subject to any disclaimer, the term of this patent is extended or adjusted under 35 U.S.C. 154(b) by 309 days.

(21) Appl. No.: 12/661,939

(22) Filed: Mar. 24, 2010

(65) Prior Publication Data

US 2011/0239339 P1 Sep. 29, 2011

(51) Int. Cl.
*A01H 5/00* (2006.01)

(52) U.S. Cl. ..... Plt./311
(58) Field of Classification Search ..... Plt./311
See application file for complete search history.

(56) References Cited

OTHER PUBLICATIONS

UPOV ROM GTITM Computer Database, GTI Jouve Retrieval Software 2011/10 Citation for 'SPCDW0902'.*

* cited by examiner

*Primary Examiner* — Wendy C Haas

(57) ABSTRACT

A new and distinct *Vanda* hybrid cultivar named 'SPCDW0902' is disclosed, characterized by white flowers, durable foliage, overall, compact plant habit and unusual low temperature tolerance. The new variety is a *Vanda*, and is normally used as an ornamental plant.

1 Drawing Sheet

Latin name of the genus and species: *Vanda* hybrid.
Variety denomination: 'SPCDW0902'.

BACKGROUND OF THE INVENTION

The new cultivar was discovered as a chance, naturally occurring mutation of the unpatented proprietary variety *Vanda* hybrid 'SPCDW0703.' The inventor, Mr. Thumrong Suphachadiwong, a citizen of Thailand, discovered the new variety as a chance mutation among a population of plants of 'SPCDW0703' at a commercial laboratory in Chonburi, Thailand. The new variety was discovered in 1993 by the inventor.

Asexual reproduction of the new cultivar 'SPCDW0902' by meristem tissue culture was performed at a commercial laboratory in Chonburi, Thailand in 2004. Since that time, multiple generations have been reproduced, and have shown that the unique features of this cultivar are stable and reproduced true to type through successive generations.

SUMMARY OF THE INVENTION

The cultivar 'SPCDW0902' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW0902.' These characteristics in combination distinguish 'SPCDW0902' as a new and distinct *Vanda* hybrid cultivar:

1. Compact overall plant.
2. White flowers.
3. Foliage with durability to resist breaking.
4. Unusual low temperature tolerance.

PARENT COMPARISON

Plants of the new cultivar 'SPCDW0902' are similar to plants of the parent variety unpatented *Vanda* hybrid 'SPCDW0703' in most horticultural characteristics. However, plants of the new cultivar 'SPCDW0902' produce white colored flowers compared to the blue flowers of the parent variety.

COMMERCIAL COMPARISON

Plants of the new cultivar 'SPCDW0902' are similar to plants of the unpatented commercial variety, *Vanda* hybrid 'Blue Magic' in most horticultural characteristics. However, plants of the new cultivar 'SPCDW0902' produce white flowers, whereas 'Blue Magic' produces blue and white colored flowers. Additionally, plants of the new variety are more compact, with smaller flowers and foliage that is more durable to resist breakage than 'Blue Magic.'

BRIEF DESCRIPTION OF THE PHOTOGRAPH

The accompanying photograph in FIG. 1 illustrates in full color a typical plant of 'SPCDW0902' grown in a greenhouse. The pot size is a commercial 11 cm container. The plant shown is approximately 5 years old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'SPCDW0902' plants grown in a commercial greenhouse in Honselersdijk, the Netherlands. Temperature ranged from 23° C. during the day and 19° C. at night. Light levels were at a minimum of 10,000 lux, including supplemental lighting given during naturally dark periods. During the naturally darkest days supplemental lighting of 10,000 lux was given for 16 hours per day. Measurements and numerical values represent averages of typical flowering types. No chemical or photoperiodic treatments were given.

Botanical classification: *Vanda* hybrid 'SPCDW0902.'

PROPAGATION

Type of propagation typically used: Tissue culture.

General propagation: The time needed from for the start of a mericlone to get the small plants ready for deflasking is approximately 24 months under a controlled temperature of about 26 degrees Celsius. After that period they have matured roots. Young tissue culture plantlets start to make roots after approximately 18 months in flasks.

Root description: Aerial roots only. Roots very fleshy, non-fibrous. Average length of old roots: 39.8 cm, average diameter of old roots: 2 mm. Average length of young roots: 13.9 cm, average diameter of young roots: 7 mm. Old roots coloured near RHS Yellow-Green 147B and 147C. Young roots colored near RHS Greyed-Green 190D; tip near RHS Green 144A.

PLANT

Growth habit: Monopodial, upright.

Height from foliage base to top of foliage: Average height from base (plant grown in hanging basket, so no soil line present) to top of foliage: 29.4 cm.

Height from to foliage base to top of flowers: Average height from base (plant grown in hanging basket, so no soil line present) to top of foliage: 39.1 cm.

Plant spread: Average: 38.0 cm at widest, 19.1 cm at narrowest.

Normal pot size: Hanging basket (8×8 cm square) or 11 cm.

Growth rate: Moderate, as compared to other *Vanda* varieties.

Number of leaves per plant: Average: 22.

FOLIAGE

Leaf:

*Arrangement*.—Distichous.

*Average length*.—Approximately 16.9 cm.

*Average width*.—Approximately 2.2 cm.

*Shape of blade*.—Ligulate, carinate, very slightly twisted lengthways.

*Aspect*.—Only very slightly curved.

*Apex*.—Unequal praemorse.

*Base*.—Sheathing. Sheath length: Average 1.7 cm. Sheath width: Average 1.0 cm. Sheath color: Near RHS Yellow-Green 144D.

*Margin*.—Entire.

*Texture of top surface*.—Smooth, dull.

*Texture of bottom surface*.—Smooth, dull.

*Color*.—Young foliage upper side: Near RHS Yellow-Green 146B. Young foliage under side: Near RHS Yellow-Green 146B. Mature foliage upper side: Near RHS Yellow-Green 146B. Mature foliage under side: Yellow-Green 146A.

*Venation*.—Type: Parallel. Venation coloration: Near RHS Yellow-Green 146B

Petiole: No petioles present, leaves sessile. .

FLOWERING CHARACTERISTICS

General description:

*Flower bud*.—Rate of opening: Approximately 7 days to complete opening from the stage described here. Length: Approximately 1.7 cm. Diameter: Approximately 1.3 cm. Shape: Broad ovate, spur pointing upward. Color: Near RHS N114A and N114B. Base and top (spur) lighter; RHS 145C and 145D.

*Peduncle*.—Length: Approximately 30.7 cm. Width: Approximately 0.6 cm. Aspect: Approximately 30° angle to rosette. Strength: Strong. Texture: Smooth, slightly glossy. Color: Near RHS Green 143C.

Inflorescence:

*Flowers per stem*.—Average: 11.

*Inflorescence arrangement*.—Axially placed raceme.

*Inflorescence height*.—Approximately 18.7 cm.

*Inflorescence width*.—Approximately 15.5 cm.

Individual flowers:

*Flower type*.—Zygomorphic (orchidaceous), typical shape for the genus *Vanda*.

*Shape*.—Zygomorphic, consisting of three sepals and three petals, one of which is transformed into a labellum (lip).

*Length*.—Approximately 8.7 cm.

*Width*.—Approximately 9.0 cm.

*Depth*.—Approximately 2.1 cm.

*Fragrance*.—No fragrance.

*Persistent*.—No.

*Quantity of petals*.—3 organized: 2 regular petals and 1 labellum (lip), described separately.

Petals:

*Arrangement*.—One lateral petal on each side.

*Length*.—Approximately 4.4 cm.

*Width*.—Approximately 3.6 cm.

*Shape*.—Obovate to short spatulate.

*Apex*.—Rounded.

*Base*.—Cuneate.

*Margin*.—Entire.

*Texture*.—Upper forward surface: Smooth, dull.

*Texture*.—Lower back surface: Smooth, very slightly glossy.

*Color*.—When opening, forward surface: Near White N155A. When opening, back surface: Near 155C, margined Green-White 157B. Fully Opened, forward surface: Near White N155A. Fully Opened, back surface: Between white 155C to 157C. Fading, forward surface: Not fading. Fading, back surface: Not fading. Color Venation Fully Opened, forward surface: Near White N155A. Color Venation Fully Opened, back surface: Between white 155C to 157C.

Labellum/lip:

*Shape*.—Three-lobed, lateral lobes involute, central lobe bi-lobed, with revolute margins.

*Length*.—Approximately 1.8 cm.

*Width*.—Approximately 1.1 cm.

*Texture*.—Smooth, dull, with 3 callosities.

*Tip*.—Bi-lobed.

*Base*.—Cuneate.

*Color*.—When opening, forward surface: lateral lobes a color between RHS Yellow-Green 145C and 150C, center near Greyed-Purple 186C; central lobe (including callosities) Yellow-Green 144C, base of central lobe Yellow Green N144B. When opening, back surface: Lateral lobes near RHS Yellow-Green 150C; central lobe near Yellow-Green. 145A, base of central lobe Yellow-Green 145D. Fully Opened, forward surface: Lateral lobes a color between RHS Yellow-Green 145C and 150C, center Greyed-Purple 186C; central lobe (including callosities) 144D, base of central lobe 145C. Fully Opened, back surface: Lateral lobes Yellow-Green 150D and lighter; central lobe Yellow-Green 145C, base of central lobe 145D and lighter. Fading, forward surface: Not fading. Fading, back surface: Not fading. Color Venation Fully Opened, forward surface: No venation visible on labellum. Color Venation Fully Opened, back surface: No venation visible on labellum.

*Margin*.—Entire.

Spurs:

*Quantity*.—Average: 1.

*Appearance*.—Short triangular, in line with central lobe of labellum.

*Length*.—Approximately 0.9 cm.

*Width*.—Approximately 0.25 cm.

*Height*.—Approximately 0.5 cm.

*Shape*.—Short triangular.

*Apex*.—Obtuse.

*Base*.—Broad cuneate.

*Margin*.—Entire.

*Texture*.—Smooth, slightly glossy.

*Color*.—Near RHS White N155C and N155D, tip near Yellow-Green 145D.

Sepals:

*Quantity*.—Average: 3.

*Appearance*.—One dorsal sepal (pointing upright) and two lateral sepals.

*Length*.—Approximately 4.4 cm.

*Width*.—Dorsal sepal approximately 3.8 cm. Lateral sepals approximately 4.3 cm.

*Shape*.—Obovate.

*Apex*.—Rounded.

*Base*.—Cuneate.

*Margin*.—Entire.

*Texture*.—Smooth, dull.

*Color*.—Near RHS N155A.

Pedicels:

*Length*.—Approximately 5.2 cm.

*Diameter*.—Approximately 0.4 cm.

*Angle*.—Approximately 75° angle to peduncle.

*Strength*.—Very strong.

*Texture*.—Smooth, axially angled with 5 "ribs", axially twisted (due to resupination), moderately glossy.

*Color*.—Near RHS White N155D, base Green-White 157D.

REPRODUCTIVE ORGANS

Stamens, style and stigma fused into column: Yes.

*Column length*.—Approximately 0.5 cm.

*Column diameter*.—Approximately 0.6 cm.

*Column color*.—Near RHS White N155C.

Ovary:

*Position*.—Inferior.

*Diameter*.—Approximately 0.4 cm.

*Color*.—Near RHS White N155D.

Pollinia color: Near RHS Yellow 17B.

OTHER CHARACTERISTICS

Disease resistance: Neither resistance nor susceptibility to normal diseases and pests of *Vanda* have been obvserved.

Drought tolerance and cold tolerance: Unusually low temperature tolerance to a minimum 6 degrees Celsius.

Fruit/seed production: Not observed to date.

What is claimed is:

1. A new and distinct cultivar of *Vanda* plant named 'SPCDW0902' as herein illustrated and described.

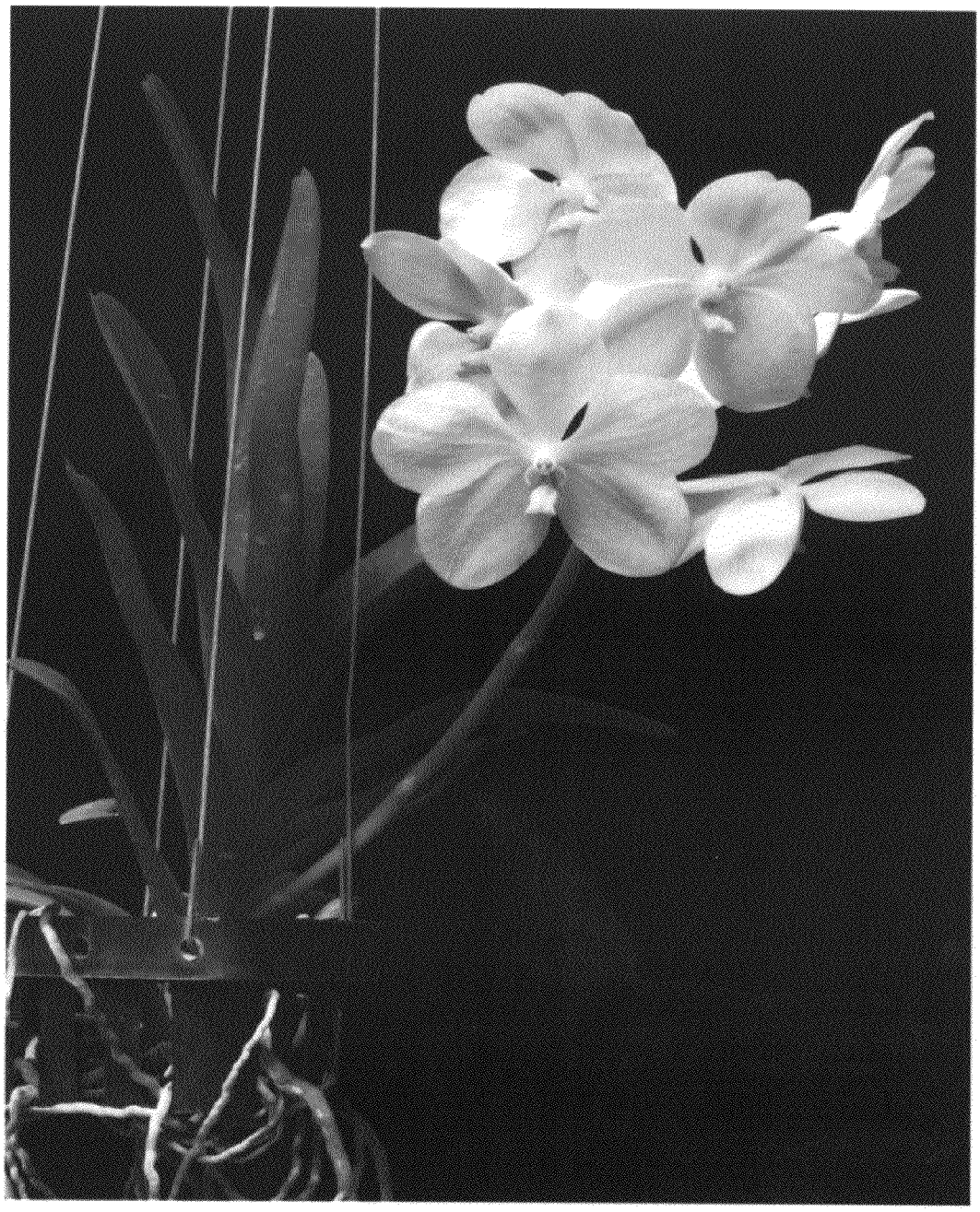

* * * * *